US006689378B1

(12) United States Patent
Sun et al.

(10) Patent No.: US 6,689,378 B1
(45) Date of Patent: Feb. 10, 2004

(54) CYCLODEXTRINS COVALENTLY BOUND TO POLYSACCHARIDES

(75) Inventors: Tong Sun, Neenah, WI (US); Jeffrey D. Lindsay, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/473,167

(22) Filed: Dec. 28, 1999

(51) Int. Cl.⁷ .......................... A61F 13/00; A61K 9/70
(52) U.S. Cl. ...................... 424/443; 536/123; 424/400; 424/401
(58) Field of Search .................. 604/359; 426/271; 162/164.1; 536/1.11, 12; 424/400, 401, 443, 445, 484, 488, 494, 78.28; 514/23, 54; 435/95

(56) References Cited

U.S. PATENT DOCUMENTS

| 2,539,704 A | 1/1951 | Schoene et al. ............ 260/231 |
| 2,827,452 A | 3/1958 | Schlenk et al. ............ 260/209 |
| 2,856,307 A | 10/1958 | Fredrickson ................ 106/208 |
| 2,917,506 A | 12/1959 | Caldwell et al. ............ 260/234 |
| 3,061,444 A | 10/1962 | Rogers et al. ................ 99/140 |
| 3,140,184 A | 7/1964 | Robbins ........................ 99/28 |
| 3,210,375 A | 10/1965 | Porret et al. ............. 260/340.7 |
| 3,222,358 A | 12/1965 | Touey et al. ................ 260/209 |
| 3,225,028 A | 12/1965 | Nordgren .................... 260/209 |
| 3,346,555 A | 10/1967 | Nordgren .................... 260/209 |
| 3,453,258 A | 7/1969 | Parmerter et al. .......... 260/209 |
| 3,553,191 A | 1/1971 | Parmerter et al. .......... 260/209 |
| 3,998,690 A | 12/1976 | Lyness et al. |
| 4,076,663 A | 2/1978 | Masuda et al. |
| 4,144,122 A | 3/1979 | Emanuelsson et al. ...... 162/158 |
| 4,357,468 A | 11/1982 | Szejtli et al. ................. 536/56 |
| 4,391,878 A | 7/1983 | Drach |
| 4,431,481 A | 2/1984 | Drach et al. |
| 4,975,293 A | * 12/1990 | Hicks et al. ................. 426/271 |
| 5,098,793 A | 3/1992 | Rohrbach et al. ........... 428/532 |
| 5,134,127 A | 7/1992 | Stella et al. .................. 514/58 |
| 5,139,687 A | 8/1992 | Borgher, Sr. et al. ........ 252/8.6 |
| 5,188,064 A | 2/1993 | House ........................ 119/172 |
| 5,207,830 A | 5/1993 | Cowan et al. .............. 106/672 |
| 5,234,610 A | 8/1993 | Gardlik et al. .............. 252/8.6 |
| 5,238,682 A | 8/1993 | Akasaka et al. ............ 424/409 |
| 5,348,667 A | 9/1994 | Bacon et al. ................ 252/8.6 |
| 5,429,628 A | * 7/1995 | Trinh et al. .................. 604/359 |
| 5,474,689 A | 12/1995 | Laughlin et al. ............. 252/8.8 |
| 5,534,165 A | 7/1996 | Piosof et al. ............... 252/8.91 |
| 5,578,563 A | 11/1996 | Trinh et al. .................. 510/513 |
| 5,660,845 A | 8/1997 | Trinh et al. .................. 424/418 |
| 5,714,445 A | 2/1998 | Trinh et al. .................. 510/103 |
| 5,718,728 A | 2/1998 | Arkens et al. ............... 8/116.1 |
| 5,728,823 A | 3/1998 | Reuscher et al. ............. 536/46 |
| 5,733,272 A | 3/1998 | Brunner et al. ............. 604/359 |
| 5,755,828 A | 5/1998 | Westland |
| 5,776,842 A | 7/1998 | Wood et al. ................. 442/394 |
| 5,782,963 A | 7/1998 | Nohr et al. ............... 106/31.27 |
| 5,783,552 A | 7/1998 | Trinh et al. .................. 510/441 |
| 5,817,332 A | 10/1998 | Urtti et al. ................... 424/149 |
| 5,830,835 A | 11/1998 | Severns et al. ............. 510/102 |
| 5,840,787 A | 11/1998 | West et al. |
| 5,871,719 A | 2/1999 | Lucas et al. ................... 424/65 |
| 5,942,217 A | 8/1999 | Woo et al. .................. 424/76.1 |
| 5,998,511 A | 12/1999 | Westland et al. |
| 6,184,271 B1 | 2/2001 | Westland et al. |
| 6,241,853 B1 | 6/2001 | Smith et al. |

FOREIGN PATENT DOCUMENTS

| DE | 40 35 378 | 5/1992 |
| EP | 0 483 380 | 11/1991 |
| EP | 0 419 434 | 5/1993 |
| EP | 0899377 A2 | 3/1999 |
| JP | 02 251681 | 10/1990 |
| JP | 11 279206 | 10/1999 |
| WO | WO 94/14888 | 7/1994 |
| WO | WO 98/22061 | 5/1998 |
| WO | WO 98/42286 | 10/1998 |
| WO | WO 99/31312 | 6/1999 |
| WO | WO 00 47811 | 8/2000 |

OTHER PUBLICATIONS

T. Tojima et al.: *Chitosan beads with pendant α–cyclodextrin: preparation and inclusion property to nitrophenolates, Carbohydrate Polymers* 40 (1999), pp. 17–22.*

Otta, et al., "Cyclodextrin Polymers as Specific Sorbents," *Proc.from the 1st Int. Symp. on Cyclodextrins*, Budapest, 1981, pp. 357–362.

Yang, et al., "Polymers of Maleic Acid as Nonformaldehyde Wrinkle–Free Finishing Agents," *Book of Papers: 1996 International Conference & Exhibition*, American Association of Textile Chemists and Colorists, pp. 160–164, Sep. 15–18, 1996.

Sarkanen, K.V. et al., "The Effects of Polyethylenimine on Some Properties of Pulp and Paper", Tappi J., Jan. 1966, pp. 4–9, vol. 49, No. 1.

Espy, H.H., "Wet–Strength Resins", Pulp and Paper Manufacture, 3$^{rd}$ ed., 1992, pp. 65–85, vol. 6.

* cited by examiner

*Primary Examiner*—Dameron L. Jones
(74) *Attorney, Agent, or Firm*—Pauley Petersen & Erickson

(57) ABSTRACT

Methods of immobilizing uncomplexed and complexed cyclodextrins to cellulose fibers and compositions including cyclodextrin immobilized to cellulose fibers are provided. The cyclodextrins are immobilized using a crosslinking means that covalently bonds the cyclodextrin to the substrate, without the cyclodextrin being derivatized. The compositions can be used in all types of cellulose fiber containing articles, such as tissues and personal care articles, for odor absorbency or for release of complexed molecules.

35 Claims, No Drawings

CYCLODEXTRINS COVALENTLY BOUND TO POLYSACCHARIDES

TECHNICAL FIELD

The invention relates to the incorporation of cyclodextrin into articles containing polysaccharides. More specifically the present invention relates to methods of immobilizing cyclodextrin onto cellulose fibers, to cellulose fibers having cyclodextrin immobilized thereon, and to articles made from such fibers.

BACKGROUND OF THE INVENTION

Numerous attempts have been made to conceal odors through the use of perfumes. Not only are such perfumes often inadequate at fully concealing odors, very often they are irritating to a user's skin. Additionally, the perfume odor itself may be irritating or offensive to a user's respiratory system and/or olfactory senses, as well as to nearby individuals.

Attempts have also been made to control odors through the use of odor absorbents. Zeolites such as those marketed under the name ABSCENTS® by Union Carbide Corporation and UOP LLC are known odor absorbers. However these solid odor absorbers, as well as activated charcoal odor absorbers, lose functionality when wet. Therefore, these odor absorbers are not preferred for applications where the article is likely to be wetted by body fluids as they lose their desired odor absorbent characteristics. Furthermore, zeolites can cause a "harsh" feel if too much is deposited onto the skin.

Cyclodextrins have been used as both perfume releasers and as odor absorbents. U.S. Pat. No. 5,660,845 to Trinh et al., for example, discloses a cyclodextrin powder useful for incorporation into an article, such as a fabric treatment sheet. U.S. Pat. No. 5,783,552 to Trinh et al., for example, discloses uncomplexed cyclodextrins incorporated into an article in the form of particles or releaseably attached to a substrate, for odor absorption.

Cyclodextrins are cyclic carbohydrates that can be produced enzymatically from starch, are generally safe for humans, and are non-polluting. In general, cyclodextrins include glucose units arranged in a donut-shaped ring. The specific coupling and conformation of the glucose units give the cyclodextrins a rigid, conical molecular structure with a hollow interior of a specific volume. Cyclodextrins thus offer a toroidal geometry with a hydrophilic exterior, which allows the cyclodextrin to dissolve in water. The "lining" of the internal cavity is formed by hydrogen atoms and glycosidic bridging oxygen atoms. This interior surface, therefore, is fairly hydrophobic.

Cyclodextrins have useful chemical properties often tied to the inclusion of chemicals in the toroidal cavity. This cavity can be filled with all or a portion of an organic molecule with suitable size to form an "inclusion complex." The association of the molecule with the cyclodextrin isolates the molecule from the aqueous solvent and may increase the molecule's stability and water solubility, since the solubility of the cyclodextrin is often higher than the solubility of the molecule. Accordingly, cyclodextrins can be used to releaseably complex chemicals, such as perfumes, drugs, flavors, insecticides, odor-mitigating chemicals, skin wellness compounds, and the like.

The unique shape and physical-chemical properties of the cavity also enable cyclodextrin molecules to absorb (form inclusion complexes with) organic molecules or parts of organic molecules which can fit into the cavity. Many odorous molecules can fit into the cavity including many malodorous molecules and perfume molecules. Therefore, cyclodextrins, and especially mixtures of cyclodextrins with different size cavities, can be used to control odors caused by a broad spectrum of organic odoriferous materials, which may or may not contain reactive functional groups.

Cyclodextrin complexes have been added to cellulose-containing articles for various purposes, as described in the above referenced patents to Trinh et al. Cyclodextrin complexes have been added to such articles in the form of particles or as loose powder, which may be suitable for articles, such as fabric treatment sheets, where it is desirable for the cyclodextrin complexes to be in free form. However, when used in articles such as diapers, such particles and powders may shift away from the preferred location of the article (where it is likely to become wet) and move to areas where they are less effective for their intended purpose. This problem was addressed in U.S. Pat. No. 5,733,272 to Brunner et al. by the use of an "adhesive", in particular a water soluble binder such as polyethylene glycol (PEG), to attach the cyclodextrin/perfume complex to the moisture-receiving area of the article. However, immobilization of cyclodextrin complexes remains a problem.

Another problem with use of cyclodextrin complexes is that they can be solubilized by aqueous solutions contacting the article and be "washed" away.

It is known to derivitize cyclodextrin with reactive moieties that can in turn react with a fabric or other substrate. Particular examples known in the art include cyclodextrin reacted with epicholohydrin and chlorinated or fluorinated triazinyl compounds, which can subsequently react with cellulose. These methods typically require pretreatment of the cyclodextrin before it can be combined with cellulose, and also suffer from safety, environmental, and high reactivity issues associated with the halogenated reactants (typically chlorinated reactants).

Accordingly, what is needed is improved methods of immobilizing cyclodextrin to cellulose. What is also needed are compositions including cyclodextrins immobilized to cellulose fibers.

SUMMARY OF THE INVENTION

The present invention is directed to methods of immobilizing uncomplexed cyclodextrins and complexed cyclodextrins to polysaccharide containing substrates, such as cellulose fibers. The present invention is also directed to compositions including cyclodextrin immobilized to a substrate, such as, preferably, one containing cellulose fibers. The cyclodextrins are immobilized by covalently bonding the cyclodextrin to the substrate, without having to first derivatize or otherwise modify the cyclodextrin. The cellulose/cyclodextrin compositions can be used in all types of cellulose fiber containing articles, such as tissues and personal care articles.

In one embodiment, the compositions contain uncomplexed cyclodextrins that function as capture agents for capture of pollutants and undesired hydrophobic agents. These compositions can function for odor control, for example. In another embodiment, the compositions include complexed cyclodextrins which function as release agents for release of, for example, perfumes or other active ingredients. Such compositions can also be used for controlled delivery of pharmaceutical agents and other chemicals from the cyclodextrin to a localized area, such as with a transdermal patch.

The means of covalently bonding the cyclodextrin to the polysaccharide can comprise a crosslinking agent capable of forming an ester or hemiacetal bond with the cyclodextrin, wherein the agent desirably is chlorine free or halogen free, or, more generally, lacks a reactive halogen group. The ester or hemiacetal bond to the cyclodextrin may be formed directly with the polysaccharide, or may be formed with a polymer which in turn is bonded to the polysaccharide, preferably through another ester or hemiacetal bond. In particular, the crosslinking agent can include a polycarboxylic acid or polymer comprising multiple cyclic anhydride groups, either of which can form ester bonds between cyclodextrin and cellulose, typically in the presence of a catalyst and suitable conditions of pH and temperature. The crosslinking means can alternatively comprise added aldehyde groups on the polysaccharide, particularly dialdehyde groups, formed by oxidation of the polysaccharide prior to reaction with cyclodextrin. The aldehyde groups can react with a hydroxy group on cyclodextrin in acidic conditions to form a hemiacetal bond. Desirably, the crosslinking means enables the cyclodextrin to be covalently bonded to the polysaccharide without the need for derivitizing the cyclodextrin (specifically, without the need to add reactive functional groups to the cyclodextrin) prior to combining the cyclodextrin with the polysaccharide. Thus, in general, cyclodextrin and its derivatives can be covalently bonded to cellulose by either reacting both the cyclodextrin and the cellulose with a bridging compound such as a polymer to form covalent bonds such as ester bonds, or by introducing functional groups on cellulose such as dialdehyde groups which can then react directly with the cyclodextrin to form covalent bonds such as hemiacetal bonds.

DETAILED DESCRIPTION OF THE INVENTION

The present invention includes methods of immobilizing uncomplexed cyclodextrins and complexed cyclodextrins to polysaccharide containing substrates, such as cellulosic fiber containing substrates, using a crosslinking means that covalently bonds the cyclodextrin to the substrate. The present invention also includes compositions including uncomplexed or complexed cyclodextrin immobilized to a substrate, such as, preferably, one containing cellulose fibers.

Cyclodextrins

The term "cyclodextrin" as used herein includes any of the known cyclodextrins such as unsubstituted cyclodextrins containing from six to twelve glucose units, especially, α-, β-, and γ-cyclodextrins, and their derivatives, and mixtures thereof. The methods of the present invention do not rely on deritization of cyclodextrin, but generally can form covalent bonds with pure α-, or γ-cyclodextrin. Derivitized cyclodextrins may be used, but the crosslinking means desirably is adapted to react with a hydroxyl group on the cyclodextrin and does not require added functional groups on the cyclodextrin to immobilize the cyclodextrin to the polysaccharide.

Alpha-, β-, and γ-cyclodextrins differ from one another by the number of glucose units in their structure. Alpha-cyclodextrins have 6 glucose units arranged in a donut-shaped ring, β-cyclodextrins have 7 glucose units arranged in a donut-shaped ring, and γ-cyclodextrins have 8 glucose units arranged in a donut-shaped ring. Cyclodextrin derivatives that can be used are disclosed in the following U.S. Pat. Nos.: 3,426,011, 3,453,257, 3,453,258, 3,453,259, 3,453,260, 3,553,191, and 3,565,887 all to Parmerter et al.; U.S. Pat. No. 3,459,731 to Gramera et al.; U.S. Pat. No. 4,535,152 to Szejtii et al.; U.S. Pat. No. 4,616,008 to Hirai et al.; U.S. Pat. No. 4,638,058 to Brandt et al.; U.S. Pat. No. 4,746,734 to Tsuchiyama et al.; and U.S. Pat. No. 4,678,598 to Ogino et al.

The term "uncomplexed cyclodextrin" as used herein means that the cavities within the cyclodextrin of the composition are unfilled before the composition is used. The term "complexed cyclodextrin" as used herein means that the cavities within the cyclodextrin of the composition are filled before the composition is used.

Examples of cyclodextrin derivatives that may be of use herein are methyl-β-cyclodextrin, hydroxyethyl-β-cyclodextrin, and hydroxypropyl-β-cyclodextrin of different degrees of substitution (D.S.), available from Amaizo, Wacker Chemicals (USA), Inc., and Aldrich Chemical Company. Water-soluble derivatives are also highly desirable.

The individual cyclodextrins can also be linked together, e.g. using multifunctional agents to form oligomers, polymers, etc. Examples of such materials are available commercially from Amaizo, and from Aldrich Chemical Company. Cyclodextrin rings can also be bound together to form polymers by processes such as linking the cyclodextrin rings together with suitable multifunctional agents. For example, a poly-cyclodextrin can be formed that is crosslinked with epichlorohydrin (β-cyclodextrin/epichlorohydrin copolymers).

It may be desirable to use a mixture of cyclodextrins. Preferably at least a major portion of the cyclodextrins are (α-, β-, and γ-cyclodextrins, more preferably α- and β-cyclodextrins. Some cyclodextrin mixtures are commercially available from, e.g. Ensuiko Sugar Refining Company, Yokohama, Japan. A mixture of cyclodextrins is preferable, for example, when the composition includes uncomplexed cyclodextrins and is intended for odor absorption, since mixtures absorb body odors more broadly by complexing with a wider range of odoriferous molecules having a wider range of molecular sizes.

The complexation between cyclodextrin and odorous molecules occurs rapidly when wetted with body fluids. This is convenient for the user because the cyclodextrins, while dry, will not fill their cavities with other environmental odors that would otherwise render them less efficient for absorbing body odors. More particularly, upon solubilization of the cyclodextrins by body fluids, the isolated cavities become available to form inclusion complexes with body odor molecules. Thus, ultimately, the availability of solubilized uncomplexed cyclodextrin is essential for an effective and efficient odor control performance. Similarly, the solubilization of complexed cyclodextrin is important for the release of the complexed molecules.

The solubility of the cyclodextrin used in the composition can be adjusted by varying the amount of particular homologues in the composition. The α-, β-, and γ-cyclodextrin homologues have solubilities of 13%, 1.9% and 30%, respectively, in water at 25° C., and 109%, 25% and 198%, respectively, in water at 80° C. In general, the solubility of the cyclodextrin gradually decreases with polymerization and a polymer having a molecular weight of 10,000 or more has negligible solubility in water. Therefore, the cyclodextrins most useful in the present invention are monomers, dimers, or trimers having a molecular weight of about 3000 or less.

Cyclodextrins having small particle sizes aid in providing higher cyclodextrin surface availability for odor absorption and therefore are preferred for this embodiment. As used herein, the particle size refers to the largest dimension of the particle and to the ultimate (or primary) particles. Small particle cyclodextrins of this invention are those having a particle size of less than about 12 microns, desirably less than about 10 microns, and more desirably less than about 5 microns, typically between about 0.001 and about 10 microns, more desirably between about 0.05 and about 5 microns. A more complete description of cyclodextrins, cyclodextrin derivatives, and cyclodextrin particle sizes useful for odor absorption can be found in U.S. Pat. No. 5,429,628 to Trinh et al.

Small particles can be conveniently prepared by mechanical, e.g. grinding techniques. Cyclodextrin and/or cyclodextrin complexes with large particle sizes can be pulverized to obtain desired smaller particles of about 10 microns and less by using, e.g. a fluid energy mill. Examples of fluid energy mills are the Trost Air Impact Pulverizers, sold by Garlock Inc., Plastomer Products, Newtown, Pa.; the Micronizer fluid energy mills sold by Sturtevant, Inc., Boston, Mass.; and the Spiral Jet Mill sold by Alpine Division, MicroPul Corporation (Hosokawa Micron International, Inc.), Summit, N.J. Small particle size cyclodextrin/agent complexes are preferably prepared by mechanical methods, e.g. kneading a slurry of the cyclodextrin and the active agent.

The amount of cyclodextrin to be added to the substrate depends upon the purpose for the cyclodextrin. The amount that can be added, in terms of grams of added cyclodextrin per gram of dry fiber, can be from about 0.01 to about 0.3, more specifically from about 0.02 to about 0.2, and most specifically from about 0.02 to about 0.08. Similar amounts of cyclodextrin can be applied for applications involving release of a complexed agent as well.

Substrates

The substrate upon which the cyclodextrin is immobilized must contain functionalities to which the cyclodextrins can be attached. For example, cyclodextrins can be covalently attached to substrates containing free hydroxyl groups. Attachment is preferably via ester or hemiacetal bonds. Substrates that contain free hydroxyl groups include polysaccharides. As used herein, the term "polysaccharides" refers to cellulose and derivatives, chitosan and derivatives, starch and derivatives, and the like. In one embodiment, the substrate includes polysaccharide fibers containing free hydroxyl groups.

The term "cellulose" or "cellulosic" as used herein refers to any material having cellulose as a major constituent and more specifically, comprising at least 50 percent by weight cellulose or a cellulose derivative. Thus, the term includes cotton, typical wood pulps, cellulose acetate, cellulose triacetate, rayon, thermomechanical wood pulp, chemical wood pulp, debonded chemical wood pulp, milkweed, and the like. The term also includes synthetic cellulose fiber types including rayon in all its varieties and other fibers derived from viscose or chemically modified cellulose. The term further includes chemically treated natural cellulosic fibers such as mercerized pulps, chemically stiffened or crosslinked fibers, sulfonated fibers, and the like.

Fibers suitable for making the webs of this invention comprise any natural or synthetic cellulose fibers including, but not limited to: nonwoody fibers, such as cotton lines and other cotton fibers or cotton derivatives, abaca, kenaf, sabai grass, flax, esparto grass, straw, jute hemp, bagasse, milkweed floss fibers, and pineapple leaf fibers; and woody fibers such as those obtained from deciduous and coniferous trees, including softwood fibers, such as northern and southern softwood draft fibers; hardwood fibers, such as eucalyptus, maple, birch, aspen, or the like. Wood fibers may be prepared in high-yield or low-yield forms, may be pulped in any known method, and include draft, sulfite, groundwood, thermomechanical pulp (TMP), chemithermomechanical pulp (CTMP) and bleached chemithermomechanical pulp (BCTMP). High brightness pulps, including chemically bleached pulps, are especially desired for tissue making, but unbleached or semi-bleached pulps may also be used. Recycled fibers are included within the scope of the present invention. Any known pulping and bleaching method may be used.

In one embodiment, cyclodextrin is crosslinked to hardwood sulfite fibers, such as sulfite eucalyptus (sold under the nomenclature Saiccor 94), or softwood kraft pulp, such as from bleached northern softwood fibers sold under the nomenclature LL-19 by Kimberly-Clark.

Crosslinking Means

The immobilizing, or crosslinking, means functions to attach the cyclodextrin to the substrate by covalently bonding to both the cyclodextrin and the substrate. In one embodiment, the crosslinking means is a water soluble crosslinking reagent suitable for hygienic articles. In one embodiment, a polymeric anionic reactive compound (PARC) is used. The crosslinking agent may also function to cause inter-fiber crosslinking between individual cellulose fibers, by covalently bonding to hydroxyl groups of different cellulose fibers. In another embodiment, the crosslinking agent may also function to cause intra-fiber crosslinking within individual cellulose fibers by covalently bonding to hydroxyl groups of the same cellulose fiber.

In another embodiment, the crosslinking means comprises aldehyde groups on the cellulose itself, provided by a prior oxidation step such as by treatment with periodate solution, enzymatic treatment such as by endoglucanase, plasma or corona discharge treatment, or other known means. Dialdehyde cellulose is preferred, including 2,3-dialdehyde cellulose or other cellulosic polymers derived therefrom, including those described by K. Rahn and T. Heinze in "New Cellulosic Polymers by Subsequent Modification of 2,3-Dialdehyde Cellulose," *Cellulose Chemistry and Technology*, 32: 173–183 (1998). Dialdehyde groups on cellulose can form crosslinks with cyclodextrin under relatively mild conditions of temperature and acidity, such as a temperature of about 80° C. to 100° C. and a pH from about 3 to 6.

Useful polymeric anionic reactive compounds are compounds having repeating units containing two or more anionic functional groups that will covalently bond to hydroxyl groups of the substrate. Such compounds will cause inter-fiber crosslinking between individual substrate fibers. In one embodiment, the functional groups are carboxylic acids, anhydride groups, or the salts thereof. Suitable polymeric anionic reactive compounds are described in a commonly owned U.S. patent application Ser. No. 09/426,299 filed Oct. 25, 1999 entitled "High Wet Performance Webs Using Polymeric Reactive Compounds".

In one embodiment the repeating units include two carboxylic acid groups on adjacent atoms, particularly adjacent carbon atoms, wherein the carboxylic acid groups are capable of forming cyclic anhydrides and specifically 5-member ring anhydrides. This cyclic anhydride, in the presence of hydroxyl groups at elevated temperature, forms ester bonds with the hydroxyl groups, including hydroxyl groups on both the cyclodextrin compound and the substrate (cellulose, chitosan, or other polysaccharides). Ester bonds are particularly useful when the substrate is a cellulosic web such as tissue because ester bonds are durable in the presence of tap water and ordinary body fluids, but can be broken at elevated pH to permit repulping of the web to form an aqueous slurry of fibers. In production of tissue or other cellulosic materials, there is frequently a need to recycle material, such as material that was not produced according to specification or that encountered runnability problems, resulting in a broken web or other defects. Use of a crosslinking agent that yields ester bonds permits the cellulosic fibers to be repulped under conditions of elevated pH that are commonly encountered in repulping operations.

Polymers, including copolymers, terpolymers, block copolymers, and homopolymers, of maleic acid are especially preferred, including copolymers of acrylic acid and maleic acid. Polyacrylic acid can be useful for the present invention if a significant portion of the polymer comprises monomers that are joined head to head, rather than head to tail, to ensure that carboxylic acid groups are present on adjacent carbons.

Exemplary polymeric anionic reactive compounds include the ethylene/maleic anhydride copolymers described in U.S. Pat. No. 4,210,489 to Markofsky. Vinyl/maleic anhydride copolymers and copolymers of epichlorohydrin and maleic anhydride or phthalic anhydride are other examples. Copolymers of maleic anhydride with olefins can also be considered, including poly(styrene/maleic anhydride), as disclosed in German Patent No. 2,936,239. Copolymers and terpolymers of maleic anhydride that could be used are disclosed in U.S. Pat. No. 4,242,408 to Evani et al. Other examples of cyclic anhydride-containing or cyclic anhydride-forming copolymers which may be used according to the present invention include, but are not limited to maleic anhydride adducts of hydrogenated polymers or copolymers; alternating copolymers of maleic anhydride and alpha-olefins; copolymers of alkyl vinyl ethers and maleic anhydride; maleic anhydride modified polyolefins; and maleic anhydride adducts of ethylene/propylene/diene terpolymer (EPDM). It will be apparent to one skilled in the art, however, that other suitable polymers containing cyclic anhydride groups or cyclic anhydride-forming groups may be used in accordance with the present invention.

One class of useful polymeric reactive compounds are terpolymers of maleic acid such as commercially available terpolymers with vinyl acetate and ethyl acetate known as BELCLENE™ DP80 (Durable Press 80) and BELCLENE™ DP60 (Durable Press 60) from FMC Corporation.

The polymeric anionic reactive compound desirably has a relatively low molecular weight and thus a low viscosity to permit effective spraying onto a tissue web. The polymeric anionic reactive compound desirably is a copolymer or terpolymer to improve flexibility of the molecule relative to the homopolymer alone. Improved flexibility of the molecule can be manifest by a reduced glass transition temperature as measured by differential scanning calorimetry. Useful polymeric anionic reactive compounds according to the present invention can have a molecular weight less than about 5,000, with an exemplary range of from about 500 to 5,0000, more specifically less than about 3,000, more specifically still from about 600 to about 2,500, and most specifically from about 800 to 2000. The polymeric anionic reactive compound BELCLENE™ 80 of FMC Corp. used in the Examples below has a molecular weight of from about 800 to about 1000, according to verbal communication with the manufacturer.

In aqueous solution, a low molecular weight compound such as BELCLENE™ 80 will generally have a low viscosity, greatly simplifying the processing and application of the compound. In particular, low viscosity is especially desirable for spray application, whether the spray is to be applied uniformly or nonuniformly (e.g., through a template or mask) to the product. A saturated (50% by weight) solution of BELCENE 80, for example, has a room-temperature viscosity of about 9 centipoise, while the viscosity of a solution diluted to 2% approximately 1 central portion (only marginally greater than that of pure water) with 1% SHP catalyst present as well. In general, it is preferred that the polymeric anionic reactive compound to be applied to the paper web have a viscosity at 25° C. of about 50 centipoise or less, specifically about 10 centipoise or less, more specifically about 5 centipoise or less, and most specifically from about 1 centipoise to about 2 centipoise. The solution at the application temperature desirably should exhibit a viscosity less than 10 centipoise and more specifically less than 4 centipoise. When the pure polymeric anionic reactive compound is at a concentration of either 50% by mass in water or as high as can be dissolved in water, whichever is greater, the liquid viscosity desirably is less than 100 centipoise, more specifically about 50 centipoise or less; more specifically still about 15 centipoise or less, and most specifically from about 4 to about 10 centipoise.

As used herein, viscosity is measured with a Sofrasser SA Viscometer (Villemandeur, France) connected to a type MIVI-6001 measurement panel. The viscometer employs a vibrating rod which responds to the viscosity of the surrounding fluid. To make the measurement, a 30 ml glass tube (Corex II No. 8445) supplied with the viscometer is filled with 10.7 ml of fluid and the tube is placed over the vibrating rod to immerse the rod in fluid. A steel guide around the rod receives the glass tube and allows the tube to be completely inserted into the device to allow the liquid depth over the vibrating rod to be reproducible. The tube is held in place for 30 seconds to allow the centipoise reading on the measurement panel to reach a stable value.

Another useful aspect of the polymeric anionic reactive compounds of the present invention is that relatively high pH values can be used when the catalyst is present, making the compound more suitable for neutral and alkaline papermaking processes and more suitable for a variety of processes, machines, and fiber types. In particular, polymeric anionic reactive compound solutions with added catalyst can have a pH above 3, more specifically above 3.5, more specifically still above 3.9, and most specifically of about 4 or greater, with an exemplary range of from 3.5 to 7 or from 4.0 to 6.5. In many embodiments, the polymeric anionic reactive compound does not require the subsequent addition of fixed base to neutralize the acidic groups.

When an acid-containing polymeric anionic reactive compound is used as the crosslinking agent with cyclodextrin, the resulting material can have synergistic benefits for use in absorbent articles because, without wishing to be bound by theory, it is believed that the remaining unreacted acid groups in the cured polymer can absorb ammonia while the cyclodextrin can absorb other odiferous compounds. Thus cellulose joined covalently to cyclodextrin via a crosslinking agent comprising a polymeric anionic reactive compound comprising polymaleic acid or monomers capable of forming acid anhydrides can be particularly useful in diapers, incontinence articles, sanitary napkins, bedpads, ostomy bags, and the like where a plurality of odiferous compounds are likely to be present in use, at least one of which is basic in nature such that it can be absorbed by acid groups, and at least one of which can form a complex with cyclodextrin.

The polymeric anionic reactive compounds of the present invention can yield wet:dry tensile ratios much higher than traditional wet strength agents, with values reaching ranges as high as from 40% to 85%, for example.

Catalysts

A suitable catalyst is one that increases the rate of bond formation between the crosslinking means and the substrate and/or the cyclodextrin. Preferred catalysts to promote covalent bonding between a PARC, cyclodextrin, and cellulose include alkali metal salts of phosphorous containing acids such as alkali metal hypophosphites, alkali metal phosphites, alkali metal polyphosphonates, alkali metal phosphates, and alkali metal sulfonates. Particularly preferred catalysts include alkali metal polyphosphonates such as sodium hexametaphosphate, and alkali metal hypophosphites such as sodium hypophosphite. Several organic compounds are known to function effectively as catalysts as well, including imidazole (IMDZ) and triethyl amine (TEA). Without wishing to be bound by theory, both imidazole and triethyl amine, like other basic catalysts, are believed to function by favorably modifying the pH of the system. Inorganic compounds such as aluminum chloride and organic compounds such as hydroxyethane diphosphoric acid can also promote crosslinking.

Other specific examples of effective catalysts are disodium acid pyrophosphate, tetrasodium pyrophosphate, pentasodium tripolyphosphate, sodium trimetaphosphate, sodium tetrametaphosphate, lithium dihydrogen phosphate, sodium dihydrogen phosphate and potassium dihydrogen phosphate.

When a catalyst is used to promote bond formation, the catalyst is typically present in an amount in the range from about 5 to about 100 weight percent of the PARC. Preferably, the catalyst is present in an amount of about 25 to 75 percent by weight of the PARC, most preferably about 50% by weight of the PARC.

Complexed Compounds

The cyclodextrin/cellulose compositions can be used "empty" or uncomplexed, to absorb chemicals from their environment, such as hydrophobic compounds released from urine, for example. Alternatively, the compositions can be used complexed to a compound so that the complex releases the compound, preferably over a period of time. As used herein, "complexed agents" or "complexed molecules" are compounds that form inclusion complexes with a cyclodextrin, and preferably are compounds which are attracted to the hydrophobic interior of cyclodextrin such that the compounds are selectively complexed with cyclodextrin rather than with cellulose. Generally, the complexed agent is selected for a particular function such as providing a desirable odor or other benefit in response to a change in environmental conditions, such as becoming wetted. Many different compounds can be complexed by cyclodextrin and used in the compositions described herein. Examples include perfumes, flavors, pharmaceuticals such as antibacterial agents, and other chemicals.

The complexed chemical can be a perfume, so that the composition provides a "scent signal" in the form of a pleasant odor which signals the removal of malodor from the article or its environment. In this embodiment, the composition includes both uncomplexed cyclodextrin and perfume complexed cyclodextrin. In other embodiments, the composition serves to release perfume only, does not serve as an odor absorber, and will thus include only perfume complexed cyclodextrin.

The scent signal is designed to provide a fleeting perfume scent, and is not designed to be overwhelming or to be used as an odor masking ingredient. When perfume is added as a scent signal, it is typically added only at very low levels, e.g. from about 0.001% to about 0.5%, preferably from about 0.003% to about 0.3%, more preferably from about 0.005% to about 0.2%, by weight of the complex composition. In order to reserve an effective amount of cyclodextrin molecules for odor control, perfume is typically present at a level wherein less than about 90% of the cyclodextrin complexes with the perfume, preferably less than about 50% of the cyclodextrin complexes with the perfume, more preferably, less than about 30% of the cyclodextrin complexes with the perfume, and most preferably, less than about 10% of the cyclodextrin complexes with the perfume.

Many types of perfumes can be used in the compositions of the present invention. There are however, perfume characteristics which are preferred for use on fabrics in order to provide a fresh fabric impression, perfume characteristics which are preferred for household use, and perfume characteristics which are preferred for use in personal care items such as diapers and sanitary napkins. Moreover, selection of the perfume will depend upon what type of release is desired, whether it be immediately upon contact with a fluid or over a period of time.

Useful perfumes include aromatic and aliphatic esters having molecular weights from about 130 to about 250; aliphatic and aromatic alcohols having molecular weights from about 90 to about 240; aliphatic ketones having molecular weights from about 150 to about 260; aromatic ketones having molecular weights from about 150 to about 270; aromatic and aliphatic lactones having molecular weights from about 130 to about 290; aliphatic aldehydes having molecular weights from about 140 to about 200; aromatic aldehydes having molecular weights from about 90 to about 230; aliphatic and aromatic ethers having molecular weights from about 150 to about 270; and condensation products of aldehydes and amines having molecular weights from about 180 to about 320; and essentially free from nitromusks and halogenated fragrance materials.

It may be preferred to include perfumes with highly volatile ingredients (boiling points of 250° C. or lower) or perfumes with moderately volatile ingredients (boiling points 250° C. to 300° C.) if the desire is to have fleeting scent.

Examples of highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, paracymene, decanal, dihydrolinalool, dihydromyrcenol, dimethyl phenyl carbinol, equcalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta terpineol, terpinyl acetate, and vertenex (para-tertiary-butyl cyclohexyl acetate). Some natural oils also contain large percentages of highly volatile perfume ingredients. For example, lavandin contains as major components linalool, linalyl acetate, geraniol, and citronellol. Lemon oil and orange terpenes both contain about 95% of d-limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

There are many references describing complexation of other chemicals, such as pharmaceuticals, with cyclodextrin. Drugs that have been suggested for complexation include those described in U.S. Pat. No. 4,727,064 to Pitha. The drugs described therein include ibuprofen, acetylsalicylic acid (or its salts), acetamidophen, apomorphine, butylated hydroxytoluene, chlorthalidone, cholecalciferol, dexamethasone, dicumarol, digoxin, diphenylhydantoin, estradiol, estriol, ethinylestradiol-3-methyl ether, ethisterone, furosemide, hydroflumethiazide, indomethacin, iproniazid phosphate, 17-methyltestosterone, nitroglycerin, norethindrone, oubain, oxprenolol, progesterone, retinal, trans-retinoic acid and/or its salts, retinol, spironolactone, sulpiride, testosterone, theophylline, aryclovir, and cloridine HCl.

Other examples are described in the following patents: U.S. Pat. No. 3,816,393, Hayashi et al. (prostaglandins for use as pharmaceuticals); U.S. Pat. No. 3,846,551, Mifune et al. (insecticide and acaricidal compositions); U.S. Pat. No. 4,024,223, Noda et al. (menthol, methyl salicylate, etc.); U.S. Pat. No. 4,073,931, Akito et al. (nitroglycerin); U.S. Pat. No. 4,228,160, Szjetli et al. (indomethacin); U.S. Pat. No. 4,268,501, Kawamura et al. (anti-asthmatic actives); U.S. Pat. No. 4,365,061, Szejtli et al. (strong inorganic oxyacids complexes); U.S. Pat. No. 4,371,673, Pitha (retinoids); U.S. Pat. No. 4,380,626, Szejtli et al. (hormonal plant growth regulator); U.S. Pat. No. 4,438,106, Wagu et al. (long chain fatty acids useful to reduce cholesterol); U.S. Pat. No. 4,474,822, Sato et al. (tea essence complexes); U.S. Pat. No. 4,529,608, Szejtli et al. (honey aroma); U.S. Pat. No. 4,596,795, Pitha (sex hormones); U.S. Pat. No. 4,616,008, Hirai et al. (antibacterial complexes); U.S. Pat. No. 4,636,343, Shibanai (insecticide complexes); U.S. Pat. No. 4,663,316, Ninger et al. (antibiotics); U.S. Pat. No. 4,675,395, Fukazawa et al. (hinokitiol); U.S. Pat. No. 4,732,759 and U.S. Pat. No. 4,728,510, Shibanai et al. (complexes of bath additives); and U.S. Pat. No. 4,751,095, Karl et al. (aspartame).

As one example, a cyclodextrin complex of a pharmaceutical can be immobilized onto the cellulose fibers of a cellulose fiber containing article to provide release of that pharmaceutical when the article is used. For example, an antibacterial agent can be released as a diaper is used to discourage the growth of bacteria on the diaper, either during or after use. As another example, a pharmaceutical agent/cyclodextrin complex can be immobilized on a cellulose based pad for use in transdermal delivery of that agent. As another example, an insecticide/cyclodextrin complex can be immobilized onto a cellulose containing material to provide protection against insects to a substance contained within or by the cellulose containing material.

Other Ingredients

Cyclodextrins crosslinked to another polysaccharide can also be used, where the polysaccharide backbone may be retained by hydrogen bonds or by crosslinking reactions as well. Polysacharides such as additional cyclodextrins, starches, and chitosans, and derivatives thereof can be used. Many other ingredients can be included in the compositions of the invention, depending upon the use of the uncomplexed or complexed cyclodextrin.

Methods of Making the Compositions

Generally, the agent is complexed with the cyclodextrin after the cyclodextrin has been covalently bonded to the substrate. Formation of the cyclodextrin complex can be done by exposing the cyclodextrin to the agent as a gas, a liquid or in solution, followed by removal of the bulk phase to leave the agent selectively retained in the cyclodextrin, or by other methods known for formation of cyclodextrin complexes described below, with the proviso that the tissue or other polysaccharide substrate will generally be present as the complex is formed. For example, methods based on solvation will employ the agent as a solute in alcohol, water, or other solvent, and the cyclodextrin will not be solubilized but will be present on the wetted tissue to form a complex with the agent. After complexation, the solution can be removed from the tissue/cyclodextrin and the tissue/cyclodextrin can be washed in an appropriate medium, mechanically agitated, or evaporated, as appropriate, to remove much of the free agent from the fibers without removing the complexed agent.

Methods of making cyclodextrin complexes are well known to those skilled in the art, including as described in the following patents: U.S. Pat. No. 5,733,272, Bruner et al. (moisture-activated encapsulated perfume); U.S. Pat. No. 4,348,416, Boden (flavoring material for use in chewing gum, dentifrices, cosmetics, etc.); U.S. Pat. No. 4,265,779, Gandolfo et al. (suds suppressors for use in detergent compositions); U.S. Pat. No. 3,816,393, Hayashi et al. (prostaglandins for use as pharmaceuticals); U.S. Pat. No. 3,846,551, Mifune et al. (insecticidal and acaricidal compositions); U.S. Pat. No. 4,024,223, Noda et al. (menthol, methyl salicylate, etc.); U.S. Pat. No. 4,073,931, Akito et al. (nitroglycerin); U.S. Pat. No. 4,228,160, Szjetli et al. (indomethacin); U.S. Pat. No. 4,268,501, Kawamura et al. (anti-asthmatic actives); U.S. Pat. No. 4,365,061, Szejtli et al. (strong inorganic oxyacids complexes); U.S. Pat. No. 4,371,673, Pitha (retinoids); U.S. Pat. No. 4,380,626, Szejtli et al. (hormonal plant growth regulator); U.S. Pat. No. 4,438,106, Wagu et al. (long chain fatty acids useful to reduce cholesterol); U.S. Pat. No. 4,474,822, Sato et al. (tea essence complexes); U.S. Pat. No. 4,529,608, Szejtli et al. (honey aroma); U.S. Pat. No. 4,596,795, Pitha (sex hormones); U.S. Pat. No. 4,616,008, Hirai et al. (antibacterial complexes); U.S. Pat. No. 4,636,343, Shibanai (insecticide complexes); U.S. Pat. No. 4,663,316, Ninger et al. (antibiotics); U.S. Pat. No. 4,675,395, Fukazawa et al. (hinokitiol); U.S. Pat. No. 4,732,759 and U.S. Pat. No. 4,728,510, Shibanai et al. (complexes of bath additives); and U.S. Pat. No. 4,751,095, Karl et al. (aspartame). Processes for the production of cyclodextrins and complexes are also described in U.S. Pat. No. 3,812,011, Okada, et al.; U.S. Pat. No. 4,317,881, Yagi, et al.; U.S. Pat. No. 4,418,144, Okada, et al.; and U.S. Pat. No. 4,378,923, Ammeraal. Disclosures of complex formation can also be found in Atwood, J. L., J. E. D. Davies & D. D. MacNichol, (Ed.): Inclusion Compounds, Vol. III, Academic Press (1984), especially Chapter 11; Atwood, J. L. and J. E. D. Davies (Ed.): Proceedings of the Second International Symposium of Cyclodextrins Tokyo, Japan, (July, 1984); and J. Szejtli, Cyclodextrin Technology, Kluwer Academic Publishers (1988).

For example, methods involving the following techniques can be used: spray drying, freeze drying, kneading, coprecipitation, grinding, and melting methods. In general, the cyclodextrin and the molecule to be complexed are brought together as a solution in a suitable solvent, preferably water, or in suspension, or by kneading the ingredients together in the presence of a suitable, preferably minimal, amount of solvent, preferably water. Other polar solvents such as ethylene glycol, propylene glycol, diethylene glycol, triethylene glycol, 2-methoxy ethanol, 2-ethoxy ethanol, glycerine, dimethylsulfoxide, dimethylformamide, 1,2-propanediol, ethanol, methanol, isopropanol, etc., and mixtures of said polar solvents with themselves and/or with water can be used as solvents for complex formation. The use of such solvents in complex formation has been disclosed in an article in Chemistry Letters by A. Harada and S. Takahashi, pp. 2089–2090 (1984). The suspension/kneading method is particularly desirable in some cases because less solvent is needed and therefore less separation of the solvent from the product is required. Other equivalent mechanical processes, e.g. milling, extrusion, etc., which require only small amounts of water and/or which result in very small particle sizes are also desirable.

In general, cyclodextrin complexes have a molar ratio of complexed compound to cyclodextrin of 1:1. However, the molar ratio can be either higher or lower, depending on the molecular size of the compound and the identity of the cyclodextrin compound. The molar ratio can be determined easily by forming a saturated solution of the cyclodextrin and adding the compound to form the complex. In general the complex will precipitate readily. If not, the complex can usually be precipitated by the addition of electrolyte, change of pH, cooling, etc. The complex can then be analyzed to determine the ratio of compound to cyclodextrin.

While the general ratio is 1:1, the ratio is determined by the size of the cavity in the cyclodextrin and the size of the active molecule. Complexes can be formed between one molecule of active and two molecules of cyclodextrin when the active molecule is large and contains two portions that can fit in the cyclodextrin. Highly desirable complexes can be formed using mixtures of cyclodextrins since some actives like perfumes and flavor extracts are normally mixtures of materials that vary widely in size.

The rate of release of complexed agents from the cyclodextrin-cellulose composition is dependent upon several factors, including the volatility of the complexed agent, the size of the agent, and the solubility of the cyclodextrin.

The following description is related to attachment of cyclodextrin to cellulose but is applicable to its attachment to other substrates as well. In general, the cyclodextrin, the crosslinking agent, and the cellulose fibers are combined and the crosslinking agent is then cured, causing it to covalently bond to the cyclodextrin and to the cellulose molecules. The cyclodextrin and crosslinking agent can be combined first and then applied to the cellulose fibers or the cyclodextrin, crosslinking agent, and cellulose can be combined in the same step. In one embodiment, an aqueous solution containing the cyclodextrin, the crosslinking agent, and a catalyst is applied to the cellulose fibers that are then exposed to conditions to cure the crosslinking agent. Accordingly, the attachment of the cyclodextrin to the substrate is accomplished in a single step.

This method allows cyclodextrin to be crosslinked to cellulose in fewer steps than other methods based on first derivitizing cyclodextrin and then crosslinking the derivitized cyclodextrin with cellulose. For example, a polymeric anionic reactive compound in solution can be combined with cyclodextrin in solution or in solid form and applied to a polysaccharide substrate, allowing crosslinking of the cyclodextrin to the substrate via the crosslinking means to occur in a single curing step, typically at elevated temperature of between about 80° C. and 170° C., depending on the crosslinking means and the catalyst that are used.

In one embodiment, the crosslinking agent will also function to cause inter-fiber crosslinking between individual cellulose fibers, by covalently bonding to hydroxyl groups of different cellulose fibers. In another embodiment, the crosslinking agent will also function to cause intra-fiber crosslinking within individual cellulose fibers, by covalently bonding to hydroxyl groups of the same cellulose fiber.

In one embodiment, the solution is applied to a fibrous web including cellulose fibers. A fibrous web is generally a random plurality of fibers that can, optionally, be joined together with a binder. Any cellulose fibers, as previously defined, or mixtures thereof, as well as other types of fibers, may be used. The cellulose fibers can alternatively be provided in free form, in a batt of comminuted wood pulp fluff, a tissue layer, a hydroentangled pulp sheet, a woven sheet, a nonwoven sheet, a tow, or a mechanically softened pulp sheet.

Suitable paper webs include tissue webs that have been creped or are intended for creping, and wet-pressed or through-dried webs in general, such as those of U.S. Pat. No. 5,637,194 to Ampulski et al., U.S. Pat. No. 4,529,480 to Trokhan, and U.S. Pat. No. 4,440,597 to Wells et al. Other suitable webs include those that are uncreped, such as those of U.S. Pat. No. 5,772,845 to Farrington, Jr. et al.

Dry airlaid webs can also be treated with cyclodextrin. For example, cyclodextrin may be crosslinked to cellulose in an airlaid web with a polymeric anionic reactive compound solution either present in a cyclodextrin solution or applied separately from application of cyclodextrin solution to the web. Airlaid webs can be formed by any method known in the art, and generally comprise entraining fiberized or comminuted cellulosic fibers in an air stream and depositing the fibers to form a mat. The mat may then be calendered or compressed, before or after treatment with a polymeric anionic reactive compound, using known techniques, including those of U.S. Pat. No. 5,948,507 to Chen et al. Following curing of the polymeric anionic reactive compound, the airlaid web may be used as a wipe, incorporated into an absorbent article such as a diaper, or used in other products known in the art.

The web can be formed with normal papermaking techniques, wherein a dilute aqueous fiber slurry is disposed on a moving wire to filter out the fibers and form an embryonic web which is subsequently dewatered by combinations of units including suction boxes, wet presses, through drying units, Yankee dryers, and the like. Examples of known dewatering and other operations are given in U.S. Pat. No. 5,656,132 to Farrington et al.

The slurry desirably has a fiber consistency of about 1 percent or greater, more desirably about 5 percent or greater, more desirably about 10 percent or greater, more desirably about 20 percent or greater. A preferred range is from about 5 percent to about 50 percent, most desirably from about 10 percent to about 30 percent.

Any of the techniques known to those skilled in the papermaking art for drying wet fibrous webs can be used.

Typically, the web is dried by applying a heated gas around, over, or through the web, by contacting the web with a heated surface, by applying infrared radiation, by exposure to superheated steam, by microwave or radiofrequency radiation, or by a combination of such methods. Through drying and contact with a heated drum are preferred methods of drying. Desirably the web is dried to about 60 to 100%, more desirably 70 to 96%, most desirably 80 to 95% before application of the PARC solution.

The fibrous web may be formed from a single layer or multiple layers. Both strength and softness are often achieved through layered tissues, such as those produced from stratified headboxes wherein at least one layer delivered by the headbox comprises softwood fibers while another layer comprises hardwood or other fiber types. Layered tissue structures produced by any means known in the art are within the scope of the present invention, including those disclosed by Edwards et al. in U.S. Pat. No. 5,494,554. In the case of multiple layers, the layers are generally positioned in a juxtaposed or surface-to-surface relationship and all or a portion of the layers may be bound to adjacent layers. The paper web may also be formed from a plurality of separate paper webs wherein the separate paper webs may be formed from single or multiple layers. In those instances where the paper web includes multiple layers, the entire thickness of the paper web may be subjected to application of the PARC or each individual layer may be separately subjected to application of the PARC and then combined with other layers in a juxtaposed relationship to form the finished paper web.

When a crosslinking agent is used, the cyclodextrin and crosslinking agent solution can be applied either as an online step in a continuous papermaking process along a section of a papermaking machine or as an offline or converting step following formation, drying, and reeling of a paper web.

The solution can be applied by spray, by coating technologies (e.g. blade coating such as with a commercial short-dwell coater, metered size presses, flooded nip coating, curtain coating, wire-wound rod coating, slot coating, and the like), printing technologies (gravure printing, ink jet printing, flexographic printing, offset printing, and the like), and including foam finishing, fabric fluid transferring, and roller fluid feeding.

The cyclodextrin and crosslinking agent solution is desirably added at about 50 to 200% add-on, most desirably 100% add-on, where add-on is the percent by weight of solution to the dry weight of the web. In other words, 100% add-on is a 1:1 weight ratio of solution to dry web. The final percent by weight crosslinking agent to the web is desirably from about 0.5 to 8%, more desirably from about 0.7% to 2%. The concentration of the crosslinking solution can be adjusted to ensure that the desired amount of crosslinking agent is added to the web.

The catalyst is present in the PARC solution at an amount in the range from about 5 to about 100 weight percent of the PARC. Desirably, the catalyst is present in an amount of about 25 to 75 percent by weight of the polycarboxylic acid, most desirably about 50% by weight of the PARC.

Drying of the treated fibers and curing of the crosslinking agent can be achieved in two separate steps or can be done in one process wherein evaporative water removal is followed by elevating the substrate to a temperature sufficient for curing.

The web, after treatment with the cyclodextrin and crosslinking agent solution, can be dried and cured with a variety of methods capable of bringing the crosslinking agent to a suitable temperature for curing. Desirably, the web is first dried at a temperature less than 150° C., desirably less than 120° C., more desirably less than 110° C. until the web has a dryness level of desirably about 90% or higher, more desirably about 94% or higher, and most desirably about 98% or higher. Additional energy is then applied to the web to heat the web to a suitable curing temperature. The treated web should be cured at a temperature sufficient to cause the PARC to crosslink with the cellulose fibers.

In one embodiment, this will generally be at a temperature within the range of about 150° C. to 190° C., for a period of time ranging from about 1 minute to 10 minutes, desirably from about 2 to 7 minutes.

In another embodiment, a flash curing technique is employed, wherein the web is exposed to a curing temperature generally above about 160° C., desirably in the range of about 200° C. to 350° C. and most desirably above about 220° C., in the range of about 250 to 320° C. for a time desirably under about one minute, more desirably less than about 15 seconds, more desirably under about five seconds, even more desirably under about two seconds, and most desirably under about one second.

The time required to properly cure the material will depend upon several factors, including the temperature, the nature of the PARC, the nature and amount of catalyst, and the add-on amount of the PARC.

Suitable drying methods include any known in the art, including contact with a Yankee dryer, contact with other heated drums such as steam-filled cylinders, through air drying, impingement drying, superheated steam drying, infrared drying, and the like. Useful drying methods include through air drying in which a hot gas (preferably air) passes through the web, infrared drying, and drying by conduction from a heated surface such as a Yankee dryer or an internally heated roll having combustion gases, electric elements, or induction heaters to heat the surface of the roll. Through air drying can be accomplished with a non-oxidative gas, but air is preferred for economic reasons. The drying apparatus can also combine both convective heating from hot air and radiative heat transfer, as disclosed in U.S. Pat. No. 4,336,279 to Metzger.

Suitable heating methods for the curing step include contact with heated surfaces such as gas-fired cylinders or other heated drums, infrared heating, radiofrequency heating, microwave heating if suitable dipolar compounds are present in the web to respond to microwave radiation to produce heat, and impingement heating or through-air drying with sufficiently hot air or with other heated gases such as carbon dioxide or nitrogen, which offer the advantage of reduced oxidative damage to the web. The gas should be heated to a temperature sufficient for it to raise the surface of the web to the desired curing temperature.

During many methods of curing, the web should be supported on a porous surface capable of withstanding high temperatures. Open metal wires or other metal supports are especially preferred.

Curing of the polymeric reactive compound can also be achieved by radio frequency drying if the polymer comprises abundant dipoles or if other materials are included that respond to radio-frequency radiation. For example, a variety of polymers such as copolyester binder fibers known in the nonwovens industry can be radiofrequency bonded. One example is the amorphous copolyester material CoPET-A which is used in Eastman's KODEL®410 binder fiber, according to W. Haile et al. in the article, "Copolyester Polymer for Binder Fibers," Nonwovens World, April-May 1999, pp. 120–124. This fiber requires a minimum temperature of about 132° C. for good bonding.

In another embodiment, the cyclodextrin, crosslinking agent, and cellulose fibers can be combined to form a slurry and a web formed from the slurry as described above. The web is then dried and heated to cure the crosslinking agent. Other methods can be used to combine the cyclodextrin, crosslinking agent, and cellulose fibers so that the cyclodextrin is immobilized on individual fibers that can then be formed into or incorporated into the desired article. For example, the method described in U.S. Pat. No. 5,190,563 of making individualized crosslinked fibers could be used.

By way of example, applied cyclodextrin levels can range from 0.05% to 25%, and specifically from about 0.1% to about 10%, and more specifically from about 0.5% to about 5%.

Methods of Using the Compositions

The compositions can be used in any article in which it is desired to control odors or to release perfumes, such as, for example, diapers, paper towels, bath tissue, facial tissue, wet wipes, absorbent pads, intake webs in absorbent articles such as diapers, bed pads, meat and poultry pads, feminine care pads, and the like. The compositions can form all or a portion of the cellulose in the article.

The cyclodextrin molecules can be covalently bound to the cellulose as described above. The cellulose can then be used in the article as all or a portion of the cellulose in the article. Alternatively, the cyclodextrin can be bound to the article after it has been formed. The cyclodextrin/cellulose can be incorporated homogeneously throughout the article or, if desired, can be incorporated into the article at preferred locations in the article.

The compositions can also be used for controlled delivery of drugs and other biological molecules from the cyclodextrin to a localized area, such as by incorporation of the cyclodextrin/cellulose into a transdermal patch. As one example, a cyclodextrin complex of a pharmaceutical can be immobilized onto the cellulose fibers of a cellulose fiber containing article to provide release of that pharmaceutical when the article is used. For example, an antibacterial agent can be released as a diaper is used to discourage the growth of bacteria on the diaper, either during or after use. As another example, a pharmaceutical agent/cyclodextrin complex can be immobilized on a cellulose based pad for use in transdermal delivery of that agent. As another example, an insecticide/cyclodextrin complex can be immobilized onto a cellulose containing material to provide protection against insects to a substance contained within or by the cellulose containing material.

The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLES

Example 1

All percentages are by weight unless otherwise stated. In Example 1, β-cyclodextrin was crosslinked to cellulose with a polymeric anionic reactive compound, unreacted cyclodextrin was washed off the fibers, and the bound cyclodextrin was then hydrolyzed and detected with a phenolphthalein-based method to confirm that the cyclodextrin had been covalently bound.

A cyclodextrin solution was prepared by mixing 3.57 g of β-cyclodextrin powder (β-cyclodextrin hydrate, Aldrich Chem. Co., Milwaukee, Wis., Cat. No. 85,608-8) in 100 ml of deionized water and heating while stirring until the β-cyclodextrin was dissolved. An aqueous solution was prepared containing 2% BELCLENET™ DP80 (Durable Press 80), a terpolymer of maleic anhydride, vinyl acetate, and ethyl acetate and 1% by weight of sodium hypophosphite (SHP).

Three 15-gram samples of LL-19 fiberized northern softwood bleached kraft fluff pulp (Kimberly-Clark Corp.) were obtained. Each sample was moistened with 50 ml of deionized water and 15 ml of the PARC solution. 15 ml of the β-cyclodextrin solution was added to Samples 1 and 3, while 15 ml of deionized water was added to Sample 2. The wetted samples were kneaded by hand to distribute the added liquids uniformly throughout each sample mass. Each sample was then dried at 105° C. for about 1 hour and then crosslinked at 170° C. in a non-convection oven (Baxter Scientific Products Drying Oven DX-31). The non-convection oven required longer exposure times than a convection oven. Samples 1 and 2 were heated for about 20 minutes while Sample 3 was heated for 9 minutes.

For each of the three samples, 9.36 g of the dry fibers were thoroughly rinsed in deionized water, first using 500 ml of water, followed by filtration, and then in three subsequent cycles of rinsing with 1 liter of water and filtering to recover the fibers. For each rinsing step, the fibers of the sample were immersed in the stated quantity of water in a beaker and agitated briefly, followed by filtration. The washing was to remove any unbound β-cyclodextrin on the fibers of Samples 1 and 3. Sample 2 was washed in the same manner. After washing, the dewatered fibers (about 30% consistency) were placed in 200 ml of deionized water with 1 ml of 0.1 N NaOH solution. For Sample 3, an additional 0.3 ml of NaOH was added to further promote hydrolysis of the bound β-cyclodextrin from the. cellulose. All three samples were then heated on a hot plate with periodic stirring to bring the temperature to 71° C. for about 20 minutes. For each sample, the fibers were filtered out and the filtrate recovered. About 200 ml of filtrate was recovered for each sample.

The presence of β-cyclodextrin in the filtrate of Samples 1 and 3 was determined using a method based on a publication by K. Sreenivasan, "A Filter Paper-based Sensing Element to Detect β-Cyclodextrin in Aqueous and Biological Fluid," *Journal of the Indian Chemical Society*, Vol. 74, March 1997, pp. 254–255. In this method, as modified for the present invention, pink drops of alkaline phenolphthalein solution are placed on filter paper and dried. When drops of liquid containing β-cyclodextrin are subsequently put on the pink spots, the pink color fades due to formation of an inclusion complex with phenolphthalein in the β-cyclodextrin.

Fisherbrand™ Qualitative Filter Paper P4 (7 cm diameter, Allied-Fisher Scientific, Cat. No. 09-803-6C) was used. A pink phenolphthalein solution was prepared from 1% phenolphthalein in ethanol (VWR, Chicago, Ill., Cat. No. VW3341-1) by adding 0.4 ml to 100 ml of water with 3.7 ml of 0.1 N NaOH solution. Drops of the pink liquid (about 0.06 ml per spot) were placed in four discrete spots around each filter paper and then the paper was placed in a 105° C. convection oven (Blue M Stabil-Therm™ Constant Temperature Cabinet, Blue Island, Ill.) to dry. Once dry, the pink spots should maintain their color when wetted with deionized water but should become clear when β-cyclodextrin was present in added drops of liquid. To test for the presence of cyclodextrin, a pink spot on the filter paper was wetted with 5 drops of the test liquid, with each drop being about 0.03 ml in volume. Four drops were placed around the rim of the pink spot, centered on the circumference and spaced apart at 90 degree intervals, with a fifth drop added to the center, such that the entire pink spot was wetted. When tested on pink spots on the filter paper, the filtrate for Samples 1 and 2 appeared to give the same results. The pink color remained, though it was redistributed by the wicking of the added liquid. With Sample 3, slight lightening of the pink color was evident. The filtrate for Sample 3 was concentrated by evaporating a portion of the water by heating the filtrate to 90° C. while stirring until only 70 ml were left. The concentrated solution had a pH of about 8.5. When tested on pink spots on filter paper, the pink color was largely removed. Deionized water, when tested, did not remove the pink color. The removal of the pink color by the filtrate from Sample 3 is taken as evidence for the presence of β-cyclodextrin that was hydrolyzed from cellulose, to which it had been covalently bonded with ester bonds.

| Sample | 1 | 2 | 3 |
| --- | --- | --- | --- |
| PARC/catalyst solution | 15 ml | 15 ml | 15 ml |
| β-cyclodextrin | 15 ml | 0 | 15 ml |
| Drying | 105° C., 1 hour | 105° C., 1 hour | 105° C., 1 hour |
| crosslinking | 170° C., 20 min | 170° C., 20 min | 170° C., 9 min |
| Hydrolysis | 1 ml of 0.1 N NaOH | 1 ml of 0.1 N NaOH | 1 ml of 0.1 N NaOH and 0.3 ml 0.1 N NaOH |
| phenol-phthalein test results | negative | negative | positive |

Example 2

The methods of Example 1 were followed, with some modifications in conditions. Two samples of the LL-19 fluff pulp were obtained, hereafter referred to as Sample A and Sample B, each having a mass of 10.9 grams. To each sample was added a solution comprising 25 ml of the PARC solution, 50 ml of deionized water, and 15 ml of either the -cyclodextrin solution for Sample A or deionized water for Sample B (the control). The moistened pulp was kneaded by hand to distribute the solutions evenly and the wet pulp for each sample was evenly distributed between 3 aluminum foil containers (7.5 cm diameter) and dried at 105° C. for 2.5 hours in the convection oven. Following drying, the pulp in two of the three containers for each sample was removed, having a mass of 7.0 grams per sample in each case, and cured in the Baxter Scientific Products oven at 170° C. for 9 minutes. The 7.0 g of fiber for each sample, after curing, was then washed and filtered repeatedly in 4 steps with 1 liter of water each time. During the third washing step, the pulp of each sample in 1 liter of water was allowed to sit for about 40 minutes at room temperature before filtration. The washed and filtered pulp for each sample was then placed in a 250-ml Erlenmeyer flask with 200 ml of deionized water and 1.6 ml of 0.1 N NaOH, resulting in an initial pH of about 12. The flasks were then placed on a hot plate with a magnetic stirrer and heated until the slurry began to boil vigorously. The pH after boiling was about 8.5. The pulp for each sample was then filtered and the filtrate recovered. The filtrate, with a volume of about 200 ml in both cases, was then boiled on the hotplate with magnetic stirring until the volume was 40 ml. The concentrated filtrates of Sample A and B were then tested for cyclodextrin content using the phenolphthalein method of Example 1. Sample A clearly decolored the pink spots on the filter paper, while the pink color remained when treated with the concentrated filtrate of Sample B. Thus, Sample A appears to have had -cyclodextrin crosslinked to the cellulose, which was then hydrolyzed off the cellulose at elevated temperature and pH, allowing the -cyclodextrin in the filtrate of Sample A to decolorize pink phenolphthalein spots on filter paper. Decoloration did not occur for Sample B, the control. The pH of the concentrated filtrates was about 9 in both cases. Thus, even through the concentrated filtrate of Sample A was alkaline, the phenolphthalein was decolored.

Example 3

Kimberly-Clark LL-19 northern softwood bleached kraft fibers in fiberized form were treated with 100% add-on of polymeric anionic reactive compound solution comprising 2% BELCLENE™ DP80 solution with 1% sodium hydrophosphite (SHP) catalyst, further comprising 1% β-cyclodextrin in solution. The mixture was cured at 180° C. for two minutes to promote crosslinking, and the resulting treated pulp sheet was mechanically fiberized with a picker to produce fluff pulp crosslinked to cyclodextrin. A control was prepared in the same manner but without the polymeric anionic reactive compound solution and cyclodextrin.

The treated and untreated fluff pulps were then tested for their ability to absorb ammonia gas in a closed vessel. Samples comprising 0.1 g of dry mass were placed in a 20-ml glass vial with 10 microliters of 30% ammonium hydroxide solution and the vial was sealed. The vial was then stored at room temperature for 16 hours, after which one cubic centimeter of the headspace gas was withdrawn from the vial and injected into a GC/TCD instrument for ammonia analysis. Ammonia absorption was determined relative to the GC/TCD results for measured gas taken from a control vial with no added cellulose sample, but still having the 10 microliters of 30% ammonium hydroxide solution. Untreated LL-19 fibers absorbed about 1.67 mg $NH_3$ per gram of sample, while the treated fibers absorbed about 7.5 mg $NH_3$ per gram of sample. The increase in ammonia absorption is attributed to the presence of acidic groups introduced with the polymeric anionic reactive compound added to the pulp, since cyclodextrin is unlikely to form inclusion complexes with ammonia. The ability of the polymeric anionic reactive compound to absorb ammonia, even after being cured, coupled with the ability of cyclodextrin to absorb other malodorous chemicals, could yield an absorbent material capable of effective control of multiple malodorous compounds useful in diapers and other products.

Example 4

An aqueous solution was prepared containing 2% BELCLENE™ DP80, 0.5% sodium hypophosphite (SHP), and 0.5% to 1.0% of an enzymatically produced mixture of α-, β-, and γ-cyclodextrins. The solution was sprayed on comminuted fibers of bleached northern softwood fibers sold under the nomenclature LL-19 by Kimberly-Clark, at an add-on level of 100% (one gram of solution per one gram of fiber). The wetted pulp fibers were then dried and cured at 180° C. for two minutes to promote crosslinking of the terpolymer with both the cyclodextrin and the cellulose.

Example 5

The same solution as in Example 1 was sprayed onto comminuted fibers of sulfite eucalyptus (Saiccor 94) at an add-on level of 100%.

Example 6

A β-cyclodextrin solution in deionized water was prepared by adding 1.76 g of β-cyclodextrin to 50 ml of water and heating to 146° F. while stirring. An aqueous solution of 1% BELCLENE™ DP80 and 0.5% sodium hypophosphite catalyst was prepared. A section of a commercial paper towel (Hi-Dry® by Kimberly-Clark Corp.), weighing 1.12 g, was sprayed with 1.7 g of the polymeric anionic reactive compound solution. 2.13 ml of the cyclodextrin solution was then added uniformly to the moist towel. The towel was dried at 80° C. for 15 minutes and then cured at 165° C. for 6 minutes. A second towel segment weighing 1.14 g was prepared in the same manner, but with 1.7 g of deionized water sprayed on the towel in place of the 1.7 g of polymeric anionic reactive compound solution to form a control. A second control was another section of tissue treated with 1.7 g of polymeric anionic reactive compound solution but no cyclodextrin (deionized water was added instead of cyclodextrin solution).

After heating, the tissue samples were rinsed and each was placed in 50 ml of water that was then heated to 164° F. to dissolve noncrosslinked cyclodextrin. The tissues were further rinsed in deionized water.

Example 7

In this example, cyclodextrin was reacted with dialdehyde pulp. The pulp was prepared by treating CR1654 Coosa River® southern softwood pulp from Kimberly-Clark Corp. with sodium periodate solution. 100 parts of CR1654 pulp were reacted with 15 parts of sodium periodate in 2500 parts of water and reacted at room temperature for 18 hours, then washed, filtered, and partially dewatered to a consistency of about 30%. The treated pulp had about 33.9 milliequivalents of aldehyde groups per 100 g of dry fiber. 2.85 g of the moist pulp, having about 0.9 g of dry fiber, was combined with 5 ml of deionized water to permit manual breaking up of flocculents. 1.42 g of the cyclodextrin solution of Example 3 having 0.05 g of cyclodextrin was added to the pulp. 0.23 ml of 0.1 N HCl solution was added for acid catalysis. The pulp and additives were blended and placed in a glass beaker and covered with a glass, then heated in an oven at 80° C. for 4 hours. The final dry mass of the treated fibers was 0.925 grams. These conditions were selected to promote crosslinking of the dialdehyde groups on the cellulose with the cyclodextrin (crosslinking with cellulose will also occur).

The above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patents, patent applications, and publications, are incorporated herein by reference.

What is claimed is:

1. A method of making a composition, comprising covalently attaching a cyclodextrin to a polysaccharide containing substrate with a crosslinking means, wherein the crosslinking means comprises a polymeric compound wherein at least one repeating monomer unit of the polymeric compound comprises:
   at least one cyclic anhydride group, and/or
   at least two groups selected from the group consisting of carboxylic acids and salts of carboxylic acids.

2. The method of claim 1, wherein the substrate comprises a polysaccharide selected from the group consisting of cellulose, starch, chitosan, and derivatives thereof.

3. The method of claim 1, wherein the substrate comprises cellulose fibers and the method further comprises causing inter-fiber crosslinking of the cellulose fibers.

4. The method of claim 1, wherein the substrate comprises cellulose fibers and the method further comprises causing intra-fiber crosslinking of the cellulose fibers.

5. The method of claim 1, wherein the cyclodextrin has an agent complexed thereto.

6. The method of claim 1, wherein the cyclodextrin will absorb at least one odiferous molecule.

7. The method of claim 1, wherein the crosslinking means is substantially free of reactive halogens.

8. The method of claim 1, wherein the crosslinking means is free of reactive halogens.

9. The method of claim 1, wherein the crosslinking means is substantially free of halogens.

10. The method of claim 1, wherein the crosslinking means is free of halogens.

11. The method of claim 1, wherein the repeating monomer unit comprises carboxylic acid groups that are capable of forming at least one cyclic anhydride.

12. The method of claim 1, wherein the cyclic anhydride comprises a 5-member ring anhydride.

13. The method of claim 1, wherein covalently attaching the cyclodextrin to a polysaccharide containing substrate occurs in the presence of a catalyst that increases the rate of bond formation between the crosslinking means and the substrate and/or the cyclodextrin.

14. The method of claim 1, wherein the polymeric compound is a copolymer, terpolymer, block copolymer, or homopolymer in which one of the monomers is maleic acid.

15. The method of claim 1, wherein the polymeric compound is a terpolymer of maleic acid, vinyl acetate, and ethyl acetate.

16. The method of claim 1, wherein the polymeric compound is a copolymer or terpolymer in which one of the monomers is maleic acid or maleic anhydride.

17. The method of claim 1, wherein the polymeric compound is a copolymer of an olefin and maleic anhydride, a vinyl/maleic anhydride copolymer, a copolymer of epichlorohydrin and maleic anhydride, or a copolymer of epichlorohydrin and phthalic anhydride.

18. The method of claim 1, wherein the polymeric compound has a molecular weight of less than about 5,000.

19. The method of claim 1, wherein the polymeric compound is in an aqueous solution having a viscosity at 25° C. of about 50 centipoise or less.

20. The method of claim 1, wherein the polymeric compound is in an aqueous solution having a viscosity of less than 10 centipoise at the temperature of the solution at the time it is combined with the cyclodextrin and substrate.

21. The method of claim 1, wherein an aqueous solution comprising the polymeric compound, at a concentration of either 50% by weight or as high as can be dissolved in water, whichever is greater, has a viscosity of less than 100 centipoise at 25° C.

22. A composition comprising a cyclodextrin covalently bound to a polysaccharide with a crosslinking means, wherein the crosslinking means comprises a polymeric compound wherein at least one repeating monomer unit of the polymeric compound comprises:

at least one cyclic anhydride group, and/or at least two groups selected from the group consisting of carboxylic acids and salts of carboxylic acids.

23. The composition of claim 22, wherein the repeating monomer unit comprises carboxylic acid groups that are capable of forming at least one cyclic anhydride.

24. The composition of claim 23, wherein the cyclic anhydride comprises a 5-member ring anhydride.

25. The composition of claim 22, wherein the composition is formed in the presence of a catalyst that increases the rate of bond formation between the crosslinking means and the substrate and/or the cyclodextrin.

26. The composition of claim 22, wherein the polymeric compound is a copolymer, terpolymer, block copolymer, or homopolymer in which one of the monomers is maleic acid.

27. The composition of claim 22, wherein the polymeric compound is a terpolymer of maleic acid, vinyl acetate, and ethyl acetate.

28. The composition of claim 22, wherein the polymeric compound is a copolymer or terpolymer in which one of the monomers is maleic acid or maleic anhydride.

29. The composition of claim 22, wherein the polymeric compound is a copolymer of an olefin and maleic anhydride, a vinyl/maleic anhydride copolymer, a copolymer of epichlorohydrin and maleic anhydride, or a copolymer of epichlorohydrin and phthalic anhydride.

30. The composition of claim 22, wherein the polymeric compound has a molecular weight of less than about 5,000.

31. The composition of claim 22, wherein the polymeric compound is in an aqueous solution having a viscosity at 25° C. of about 50 centipoise or less.

32. The composition of claim 22, wherein the polymeric compound is in an aqueous solution having a viscosity of less than 10 centipoise at the temperature of the solution at the time it is combined with the cyclodextrin and substrate.

33. The composition of claim 22, wherein an aqueous solution comprising the polymeric compound, at a concentration of either 50% by weight or as high as can be dissolved in water, whichever is greater, has a viscosity of less than 100 centipoise at 25° C.

34. An article comprising the composition of claim 22.

35. The article of claim 34, wherein the article is selected from the group consisting of a diaper, a sanitary napkin, a disposable wipe, and a reusable wipe.

* * * * *